United States Patent [19]

Seto

[11] Patent Number: 4,871,666

[45] Date of Patent: Oct. 3, 1989

[54] PROCESS FOR PREPARING A LIPID COMPOSITION HAVING UPON SAPONIFICATION A HIGH GAMA-LINOLENIC ACID CONTENT

[75] Inventor: Akira Seto, Yokohama, Japan

[73] Assignee: Nisshin Oil Mills, Ltd., Japan

[21] Appl. No.: 758,023

[22] Filed: Jul. 23, 1985

[30] Foreign Application Priority Data

Jul. 31, 1984 [JP] Japan ................................ 59-159275

[51] Int. Cl.$^4$ .......................... C12P 7/64; C12N 1/14; C12R 1/645
[52] U.S. Cl. .................................... 435/134; 435/254; 435/911
[58] Field of Search ................... 426/55, 60; 435/134, 435/171, 254, 911

[56] References Cited

U.S. PATENT DOCUMENTS 4,783,408 11/1988 Suzuki et al. ....................... 435/134

FOREIGN PATENT DOCUMENTS 0125764 11/1984 European Pat. Off. ............. 435/134

OTHER PUBLICATIONS

Manocha et al.; "The Effect of Growth Temperature on the Fatty Acid Composition of *Thamnidium elegans* Link"; *Can. J. Microbiol.* vol. 24, p. 670–674 (1978).

*Primary Examiner*—Elizabeth C. Weimar
*Attorney, Agent, or Firm*—Bacon & Thomas

[57] ABSTRACT

A lipid composition having a high γ-linolenic acid content is prepared by culturing mold fungi of the genus *Thamnidium* in an aqueous nutrient culture medium having a relatively high concentration of a carbon source, and the lipid composition is recovered from the cultured mold fungi.

8 Claims, No Drawings

PROCESS FOR PREPARING A LIPID COMPOSITION HAVING UPON SAPONIFICATION A HIGH GAMA-LINOLENIC ACID CONTENT

BACKGROUND OF THE INVENTION

1. Field of the Invention

The present invention relates to a process for preparing a lipid composition having a high γ-linolenic acid content and, more particularly, to a process for preparing such a composition from a specific living microorganism.

2. Description of the Prior Art 6,9,12-octadecatrienoic acid or γ-linolenic acid (to be referred to as GLA hereinafter) is a fatty acid synthesized in a living organism from linoleic acid. GLA is converted into prostaglandin $E_1$, $F_2$, $E_2$ or $F_2$ through bishomo-γ-linolenic acid. It has been found recently that the in vivo conversion reaction of linoleic acid into GLA is hindered by aging, alcohol drinking, and vitamin deficiency. An imbalance in prostaglandin due to a GLA deficiency is considered to be a factor causing allergic diseases, thrombosis, or cancer.

GLA which is therefore important to the health of living organisms is obtainable from plant seeds such as seeds of the evening primrose. However, GLA is contained in evening primrose seeds in small amounts and accounts for at most 10 % by weight of the total fatty acid content. Furthermore, plant seed oil also contains about 70 % by weight based on the total fatty acid content of linoleic acid. When GLA is obtained by refining a fatty acid mixture obtained from plant seed oil by solvent fractionation or the like, GLA cannot be easily separated from linoleic acid since the two components behave in a similar manner.

It has been proposed to obtain GLA from the lipids of microorganisms. See, for example, R.O. Mumma, Lipids, 6, 584 (1971); R. Shaw, Biochem. Biophys. Acta. 98, 230 (1965); and Suzuki et al., Yukagaku (Oil Chemistry), 30, 863, (1981). However, the GLA content of the GLA producing microorganisms mentioned in these articles is low and represents at most 10 to 20 % of the total lipid content. Japanese Patent Publication (Kokoku) No. 58-22199 reports that when mold fungi of the genus Mortierella are cultured in a medium to which a hydrocarbon is added, the cultured fungi have a GLA content of 20 % or more based on the total fatty acid content. However, mold fungi of the genus Mortierella grow at a slow rate and grow particularly slowly at a low temperature which is most conducive for them to produce GLA. Therefore, the GLA productivity of these fungi is low.

The present invention is directed to a technique for producing GLA from cultured microorganisms.

SUMMARY OF THE INVENTION

It is, therefore, an object of the present invention to provide a novel process for preparing from cultured microorganisms a lipid composition containing a high concentration of GLA.

In order to achieve the above object of the present invention, there is provided a process for preparing a lipid composition having a high y-linolenic acid content, comprising the steps of:

culturing mold fungi of the genus Thamnidium in an aqueous nutrient culture medium containing a relatively high concentration of a carbon source; and recovering the lipid composition from the cultured mold fungi.

A fatty acid composition containing a high concentration of GLA can be obtained by saponifying the thus obtained lipid composition.

DETAILED DESCRIPTION OF THE PREFERRED EMBODIMENTS

In order to determine which strains satisfy the conditions of a high lipid content, a high GLA content in the lipid and a fast growth, the present inventors screened strains from a catalogue. As a result of this screening, it was found that Thamnidium elegans (to be referred to as T. elegans hereinafter; accession numbers NRRL-1613, 2468, and 2469) best satisfied these requirements. As a result of further studies made on the basis of this finding, it was also found that mold fungi of the genus Thamnidium other than T. elegans substantially satisfy the above conditions and that culturing of such mold fungi in a specific culture medium can yield a lipid composition having a high GLA content. The present invention has thus been established.

The mold fungi of the genus Thamnidium to be used herein belong to mucorales of Zygomycetes. They have grayish white hypha and are aerobic. The appropriate temperature for growth is 25 to 30° C. More detailed explanations are given in C.W. Hesseltine et. al., Am. J. of Botany, Vol. 43, No. 9, pp 696-703, 1956.

These fungi are all deposited in NRRL at the Northern Regional Research Center of the U.S. Department of Agriculture located at 1815 North University Street, Peoria, Illinois 61604. T. elegans is particularly preferable. However, other mold fungi including Thamnidium anomalum, accession number NRRL-2465, can also be used. It has been confirmed in the art that these mold fungi of the genus Thamnidium do not produce a toxic substance such as aflatoxin.

These mold fungi can be generally cultured by static culture, shaking culture or aerated stirring culture using a liquid culture medium. The culture medium to be used is limited only in that it must contain carbon and nitrogen sources. However, a culture medium containing a relatively high concentration of a carbon source is preferably used.

An organic carbon source such as glucose or sodium acetate is preferable. Such a carbon source is contained, preferably, in the amount of 3 to 30 % by weight based on the total weight of the culture medium. More preferably, the culture medium contains such a carbon source in the amount of 5 to 15 % by weight.

A nitrogen source may be an organic nitrogen source such as yeast extract, malt extract, peptone, or urea; or an inorganic nitrogen source such as a nitrate or ammonium sulfate. Preferably, the nitrogen source is contained in the amount of 0.5 to 2 % by weight based on the total weight of the culture medium.

As has been described hereinabove, the culture medium to be used herein is an aqueous liquid culture medium. This liquid culture medium can be prepared by dissolving the carbon and nitrogen sources in water. Preferably, the liquid culture medium is weakly acidic or neutral (pH 4.0 to 6.0). When vitamins such as vitamin B6 or biotin are added in the culture medium, growth of mold fungi is facilitated. It is preferred that vitamin B6 and biotin are added to the medium in amounts of 0.1 to 0.5 mg% and 0.001 to 0.005 mg%, respectively. Other source elements may be contained in the medium. Such source elements include a phosphorus source (e.g., potassium dihydrogen phosphate), a sodium source (e.g., sodium chloride), a magnesium source (e.g., magnesium sulfate), an iron source (e.g., ferrous sulfate), a calcium source (e.g., calcium chloride), a copper source (e.g., cupric sulfate), a zinc source (e.g., zinc sulfate), or a manganese source (e.g., manganese chloride).

When mold fungi of the genus *Thamnidium* are cultured, using a culture medium as described above, the mold fungi are generally inoculated with 0.5 to 5 grams per liter of the medium. Culturing is preferably performed within a temperature range of 15 to 30° C. The culture period is 4 to 15 days.

The mold fungi cultured in this manner are recovered by filtering and the lipid content is extracted from the recovered mold fungi. Since the lipid containing GLA is not secreted in the medium during culturing, the culture medium need not be recovered.

The lipids can be extracted by adding glass beads to the recovered wet mold fungi and homogenizing the mixture with an organic solvent such as hexane or alcohol so as to allow lipids in the fungi to be transferred into the solvent. The solvent phase containing the lipids is recovered by a means such as filtering, and the desired lipids are obtained by removing the solvent from the recovered solvent phase by reduced pressure distillation or the like. The amount of the solvent used is generally about 2 to 5 times by weight that of the wet fungi. The homogenization is preferably performed at a temperature of about 10 to 20° C.

Another method can be used to extract the lipids. According to this method, the recovered wet mold fungi are freeze-dried in a temperature range of -31 20 to −40° C. Thereafter, the mold fungi are brought into sufficient contact with an organic solvent such as a mixture of hexane and isopropanol, hexane and ethanol, or chloroform and methanol so as to allow the lipids to be transferred into the solvent. Preferably, the solvent is used in the amount about 4 to 10 times the weight of the fungi. The mold fungi are brought into contact with the solvent at a temperature of, preferably, 10 to 20° C and for a time period of 1 to 3 hours. After the extraction, the solvent phase containing lipids is recovered by filtering, and the solvent is removed from the recovered solvent phase by reduced pressure distillation or the like.

A fatty acid composition which can be obtained by saponification of the lipids extracted from mold fungi of the genus *Thamnidium* cultured in this manner contains 20 % by weight or more of GLA. The fatty acid composition contains a relatively small amount of fatty acid such as linoleic acid which have physical properties similar to those of GLA. Therefore, the purification of GLA is relatively easy.

When the lipids extracted in this manner are saponified (subjected to hydrolysis), an acid (e.g., a mineral acid such as hydrochloric acid or sulfuric acid) or an alkali (e.g., sodium hydroxide or potassium hydroxide) is used in the amount of 0.25 to 0.50 parts by weight based on one part of the lipids, and saponification is performed in a suitable organic solvent (e.g., an alcohol such as methanol). The hydrolysis temperature is generally selected to be 70 to 80° C. and the hydrolysis time is selected to be 30 minutes to 2 hours. During hydrolysis, the lipids are decomposed and the fatty acids are liberated. After the unsaponified materials are extracted and removed by a nonpolar solvent such as petroleum ether and the residue is acidified, the fatty acids are extracted using an organic solvent such as petroleum ether. Extraction of the fatty acids is preferably performed within a temperature range of 10 to 20° C. After the extraction of the fatty acids, the solvent is distilled off to provide a desired fatty acid composition. As described above, this fatty acid compostion contains GLA in an amount of 20 % by weight or more. The fatty acid composition contains other fatty acid components such as palmitic acid, stearic acid, oleic acid, and linoleic acid.

Further, the GLA contained in the fatty acid composition can be further purified by the urea adduct process. For example, a mixture of one part by weight of fatty acid composition, 2 parts by weight of urea and 10 parts by weight of methanol is prepared and heated at about 60° C. The solution is allowed to stand at about 4° C. overnight. The thus treated solution is filtered to remove undissolved material including saturated and mono-unsaturated fatty acids such as palmitic, stearic and oleic acids. The filtrate contains highly unsaturated fatty acids such as linoleic acid and GLA. The evaporation of the solvent from the filtrate gives a fatty acid composition containing GLA in an amount of about 40 % by weight.

Alternatively the GLA contained in the fatty acid composition may be purified by column chromatography after the ethyl esterification. The ethyl esterification can be performed by heating a mixture of fatty acid composition (1 g), conc. sulfuric acid (0.2 g) and ethanol (10 ml) to 80° C. for 2 hrs. The fatty acid ethyl esters are extracted with petroleum ether. For the purification, a silica gel column is saturated with a first solvent mixture of hexane and ether at a ratio of 400/1 (vol./vol.). The ethyl esterified fatty acid composition is charged in the column in an amount of about 5 % by weight based on the total weight of the silica gel. Then the first solvent mixture is passed through the column. When the GLA ethyl ester begins to elute, the solvent is changed to a second solvent mixture of hexane and ether at a ratio of 8/2 (vol./vol.). The thus obtained GLA ethyl ester fraction contains 80 to 95 % by weight of GLA ethyl ester.

The fatty acid composition purified by the urea adduct process may be further purified by the above-noted column chromatography.

The GLA ethyl ester fraction obtained by the column chromatography may be subject to the saponification as described with respect to the extracted lipids to obtain free GLA. After the saponification, the saponified mixture is rendered acidic and extracted with an organic solvent such as petroleum ether. The ether phase is collected, and the solvent is removed to obtain high purity free GLA.

The present invention will now be described by way of its Examples.

EXAMPLE 1

An aqueous organic nutrient culture medium having the composition shown in Table A below was prepared.

TABLE A

| (Culture Medium Composition) | |
|---|---|
| Yeast extract | 2 g/l |
| Malt extract | 3 g/l |

TABLE A-continued

| (Culture Medium Composition) | |
|---|---|
| Peptone | 3 g/l |
| Urea | 5 g/l |
| Glucose | 100 g/l |
| Water | Balance to prepare 1 liter of composition |

0.2 grams of *T. elegans* (NRRL-1613) were inoculated in one liter of this medium and incubation was performed by shaking culture, which was done by horizontal turning at 200 rpm at 27° C. for 8 days. After culturing, the mixture was filtered to recover the fungi which were freeze-dried at −30° C. 4.0 grams of dried fungi were obtained per liter of the medium. The mold fungi were mixed with 20 grams of a solvent mixture of n-hexane and isopropanol in the ratio of 3 : 2 (Vol./Vol.) and the mixture was vigorously stirred at 10° C. The solvent phase was recovered by filtering and the solvent was distilled off by reduced pressure distillation. 0.9 grams of the lipids were thus obtained.

In order to perform saponification, 0.2 ml of a mixture of 2N NaOH and methanol was added to a portion (0.5 grams) of the lipids. The mixture was heated at 75° C. for 120 minutes in a hot water bath. After the unsaponified materials were removed, the residue was acidified, and fatty acids were extracted with hexane. Then the solvent phase was recovered, and the solvent was distilled off from the solvent phase to provide a fatty acid composition. The fatty acid composition was subjected to methyl esterification by a conventional method to analyze the fatty acid composition by gas chromatography. The analysis results were shown in Table B below.

TABLE B

| (Fatty Acid Composition) | | | | | |
|---|---|---|---|---|---|
| Fatty acid | 16:0[1] | 18:0[2] | 18:1[3] | 18:2[4] | 18:3 ($\gamma$)[5] |
| % by weight | 20.3 | 5.8 | 25.8 | 17.0 | 28.1 |

Note:
[1] Palmitic acid
[2] Stearic acid
[3] Oleic acid
[4] Linoleic acid
[5] GLA

EXAMPLE 2

An aqueous culture medium as shown in Table C below was prepared.

TABLE C

| (Culture Medium Composition) | |
|---|---|
| Yeast extract | 2 g/l |
| Ammonium sulfate | 6 g/l |
| Glucose | 70 g/l |
| Vitamin B6 | 2 mg/l |
| Biotin | 0.02 mg/l |
| Water | Balance to prepare 1 liter of composition |

1.0 grams of the *T. elegans* (NRRL-2468) was inoculated in one liter of this culture medium and incubation was performed by shaking culture at 23° C. and 200 rpm for 9 days. After culturing, the mixture was processed in the same manner as in Example 1 to yield 3.6 grams of freeze-dried fungi. The fungi were extracted in the same manner as in Example 1 to yield 0.95 grams of lipids. The fatty acid composition in the lipids was analyzed following the procedures of Example 1, and the obtained results are shown in Table D below.

TABLE D

| (Fatty Acid Composition) | | | | | |
|---|---|---|---|---|---|
| Fatty acid | 16:0 | 18:0 | 18:1 | 18:2 | 18:3 ($\gamma$) |
| % by weight | 18.0 | 6.1 | 25.8 | 22.0 | 26.0 |

EXAMPLE 3

An aqueous culture medium having the composition in Table E below was prepared.

TABLE E

| (Culture Medium Composition) | | | |
|---|---|---|---|
| Glucose | 200 g/l | Ferrous sulfate · 7H$_2$O | 30 mg/l |
| Yeast extract | 2 g/l | Calcium chloride | 300 mg/l |
| Urea | 5 g/l | Zinc sulfate · 7H$_2$O | 3 mg/l |
| Potassium dihydrogen phosphate | 10 g/l | Vitamin B6 | 6 mg/l |
| Magnesium sulfate | 2 g/l | Biotin | 0.06 mg/l |
| Sodium chloride | 0.3 g/l | Water (Balance to prepare 1 liter of composition) | |

Thirty liters of this culture medium were charged in a jar fermentor and sterilized at a temperature of 120° C. and at a pressure of 1.5 kg/cm$^2$. Thereafter, 30 grams of *T. elegans* (NRRL-2468) were inoculated in the medium and an air-blowing stirring culture was performed at 28° C. for 5 days. During culturing, 2N NaOH aqueous solution was added to maintain the pH of the medium at 4.0 or higher.

After culturing, the medium was processed in the same manner as in Example 1 to yield 1350 grams of the freeze-dried fungi. The fungi were extracted as in Example 1 to yield 430 grams of lipids.

The thus obtained lipids were saponified under the same conditions as those in Example 1 to provide 310 grams of fatty acids. The fatty acids had a composition as shown in Table F below.

TABLE F

| (Fatty Acid Composition) | | | | | |
|---|---|---|---|---|---|
| Fatty acid | 16:0 | 18:0 | 18:1 | 18:2 | 18:3 ($\gamma$) |
| % by weight | 13.0 | 9.1 | 20.8 | 28.3 | 27.6 |

According to the present invention, a lipid composition having a high GLA content can be prepared with simple procedures. Since an organic carbon source which is guaranteed to be safe such as glucose can be used, a lipid composition obtained is safe compared to a case wherein a hydrocarbon is used as the carbon source. Furthermore, as described above, mold fungi of the genus *Thamnidium* used in the present invention do not produce any toxic substances.

What is claimed is:

1. A process for preparing a lipid composition having, upon saponification, a high $\gamma$-linolenic acid content of 20% by weight or more, comprising:
   culturing mold fungi *Thamnidium elegans* NRRL-1613 or *Thamnidium elegans* NRRL-2468 in an aqueous nutrient culture medium having a relatively high concentration of a carbon source including 70–200 g/liter of glucose; and recovering the lipid composition from the cultured mold fungi, said lipid composition, upon saponification, being capable of resulting in a fatty acid composition having a γ-linolenic acid content of 20% by weight or more.

2. A process according to claim 1, wherein the culturing step is performed at a temperature of 15 to 30° C. and with a weakly acidic or neutral culture medium.

3. A process according to claim 2, wherein the culturing step is performed by shaking culture.

4. A process according to claim 2, wherein the culturing step is performed by air-blowing stirring culture.

5. A process according to claim 1, wherein the recovering step is performed by extraction using an organic solvent.

6. A process for preparing a fatty acid composition having a high γ-linolenic acid content of 20% by weight or more, comprising:
   culturing mold fungi *Thamnidium elegans* NRRL-1613 or *Thamnidium elegans* NRRL-2468 in an aqueous nutrient culture medium having a relatively high concentration of a carbon source including 70–200 g/liter of glucose;
   recovering the lipid composition from the cultured mold fungi; and
   saponifying the recovered lipid composition to liberate a fatty acid composition; and recovering the fatty acid composition.

7. A process accroding to claim 6, wherein the culturing step is performed at a temperature of 15 to 30° C. and with a weakly acidic or neutral culture medium.

8. A process according to claim 6, wherein the step of recovering the lipid composition is performed by extraction using an organic solvent.

* * * * *